United States Patent
Yin et al.

(10) Patent No.: US 9,119,568 B2
(45) Date of Patent: Sep. 1, 2015

(54) SENSING DEVICE FOR DETECTING A WEARING POSITION

(75) Inventors: Bin Yin, Eindhoven (NL); Richard Marcel Pierre Doornbos, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 645 days.

(21) Appl. No.: 13/320,818

(22) PCT Filed: May 17, 2010

(86) PCT No.: PCT/IB2010/052163
§ 371 (c)(1),
(2), (4) Date: Nov. 16, 2011

(87) PCT Pub. No.: WO2010/134010
PCT Pub. Date: Nov. 25, 2010

(65) Prior Publication Data
US 2012/0072168 A1    Mar. 22, 2012

(30) Foreign Application Priority Data
May 20, 2009   (EP) ..................................... 09160729

(51) Int. Cl.
*G01C 1/00*   (2006.01)
*A61B 5/11*   (2006.01)
*A61B 5/06*   (2006.01)
*A61B 5/00*   (2006.01)

(52) U.S. Cl.
CPC .............. *A61B 5/1118* (2013.01); *A61B 5/061* (2013.01); *A61B 5/1117* (2013.01); *A61B 5/7264* (2013.01); *A61B 2562/0219* (2013.01)

(58) Field of Classification Search
CPC ....... G06F 15/00; A61B 5/061; A61B 5/1118
USPC ......... 702/32, 39, 67, 75, 105, 116, 160, 161; 73/489–492, 510, 865.4
See application file for complete search history.

(56) References Cited

U.S. PATENT DOCUMENTS 6,941,239 B2 *   9/2005   Unuma et al. ................. 702/141
7,467,060 B2 *   12/2008  Kulach et al. ................. 702/141

(Continued)

FOREIGN PATENT DOCUMENTS

WO    2005011480 A2    2/2005

OTHER PUBLICATIONS

Yin et al: "Detection of Sensor Wearing Positions for Accelerometry-Based Daily Activity Assessment"; Proceedings of the Sixth IASTED International Conference on Biomedical Engineering, Innsbruck, Austria, February 2008, pp. 390-395.

*Primary Examiner* — Elias Desta

(57) ABSTRACT

The invention relates to sensing device for detecting the wearing position of the device with respect to a user. The device comprises a motion sensor for detecting a motion signal, a height sensor for detecting a height signal and a computing unit. The computing unit receives the motion signal and the height signal, and based thereon determines the wearing position of the sensing device with respect to the user. In embodiments, parameters related to movement of the user are extracted from the signals, and the wearing position is detected from these parameters by means of a classification algorithm.

19 Claims, 5 Drawing Sheets

(56) References Cited

U.S. PATENT DOCUMENTS

| | | |
|---|---|---|
| 7,640,135 B2 * 12/2009 | Vock et al. | 702/141 |
| 2005/0033200 A1 2/2005 | Soehren et al. | |
| 2005/0080590 A1 * 4/2005 | Kawai et al. | 702/141 |
| 2006/0161079 A1 7/2006 | Choi et al. | |
| 2006/0284979 A1 12/2006 | Clarkson | |
| 2007/0250261 A1 * 10/2007 | Soehren | 701/207 |
| 2008/0190202 A1 8/2008 | Kulach et al. | |
| 2011/0077904 A1 * 3/2011 | Jung et al. | 702/152 |

* cited by examiner

SENSING DEVICE FOR DETECTING A WEARING POSITION

FIELD OF THE INVENTION

The invention relates to sensing device for detecting the wearing position of the device with respect to a user.

BACKGROUND OF THE INVENTION

In recent years, on-body sensing has been made possible due to the technological progress within sensor miniaturization, energy saving and wireless communications. A sensing device in the form of a body-worn accelerometer-based activity monitor (AM) is able to record motion-induced acceleration signals. From such acceleration signals, activity-context information, such as physical activity related energy expenditure (AEE), activity type and durations can be extracted. In healthcare applications, the activity-context information helps to correctly interpret patients' vital body signals, such as ECG and respiration rate, and to improve the diagnosis. In consumer lifestyle applications, it enables users to maintain a healthy physical activity level, thus avoiding inactivity-related diseases.

To translate the acceleration data into an AEE value with a required accuracy or to be able to provide correct activity type recognition, it may be crucial to have prior knowledge of the sensor's location. The article: "Detection of Sensor Wearing Positions for Accelerometry-based Daily Activity Assessment", *The Sixth IASTED International Conference on Biomedical Engineering*, February 2008 by Yin and Goris, discloses a method of detecting a sensor wearing position based on comparing body position dependent features that are extracted from measured acceleration data with features of an established feature database.

FIG. 1 is adapted from the mentioned article by Yin and Goris and shows an example of correlation between the acceleration power accumulated in the form of total accelerations pr. day (y axis) and the corresponding physical activity level measured with a doubly-labeled water method (x axis). The correlation curves 1, 2, 3, which respectively result from linear regression from the experimental data 4, 5, 6, differ depending on the sensor wearing position, i.e., waist 1, 4 (diamond), wrist 2, 5 (square) and bra 3, 6 (triangle). Thus even though the readout data relate to the same activities, the determined physical activity level differ according to the attachment position of the accelerometer.

Hence, there is the need in the art for accurately detecting the wearing position of an on-body sensing device.

SUMMARY OF THE INVENTION

It is an object of the present invention to provide a flexible on-body sensing device which can be worn at a number of body position while nevertheless accurately can detect the wearing position of the device itself irrespectively of the wearing position. Moreover it is a further object of the present to provide an on-body sensing device which is able to extract the wearing location with a very limited number of user-device interactions, and even with no need of any intervention from the user during any type of activity, so as to provide a fully automatic sensing device for detecting the wearing position.

The invention preferably seeks to mitigate, alleviate or eliminate one or more of the disadvantages of the prior art singly or in any combination.

In accordance with a first aspect, there is provided a sensing device for detecting a wearing position, the device comprising:
a motion sensor for detecting a motion signal;
a height sensor for detecting a height signal; and
a computing unit;
wherein the motion sensor and the height sensor are communicatively connected to the computing unit, and where the computing unit in response to receiving the motion signal and the height signal determines the wearing position of the sensing device with respect to a user.

The inventors of the present invention have realized that in order to detect the correct wearing position with a high certainty, it is important to base the decision on more than one input signal, and where the input signals behave differently during a specific movement of the user when the sensing device is attached to different body parts. A signal related to a motion of the user and a signal related to the height of the sensor fulfill this requirement. By basing the detection of the wearing position on a motion signal and a height signal, a sensing device which accurately can determine the wearing position solely based on the detected signals and which does not require, or which does only require few, user inputs may thereby be provided. Embodiments of the present invention may therefore provide a sensing device which automatically detects the wearing position of the device.

In advantageous embodiments of the present invention, the computing unit is further adapted to recognize a preselected type of a motion in the motion signal and/or in the height signal, or at least to recognize a candidate segment of data representing the preselected type of a motion in the signals. The computing unit is further adapted to detect that a motion of the preselected type or a candidate segment of data of the preselected type is present in the motion signal and in the height signal. It is advantageous to recognize the type of motion in the detected signals since the accuracy of the detection of the wearing position can be improved by basing the detection of the wearing position on a specific type of movement of the user wearing the sensing device.

In advantageous embodiments of the present invention, the computing unit is further adapted to extract one or more parameters from the motion signal and the height signal measured during the occurrence of the motion of the preselected type, and basing the determination of the wearing position on such parameters. It is convenient to base a computational decision process on extracted parameter values and/or ranges.

In advantageous embodiments of the present invention, the detection of the wearing position is based on a classification algorithm. Classification algorithms are well-suited in connection with computational decision making based on complex input signals.

In a second aspect, the invention relates to a method of detecting a wearing position of a sensing device, where the detection of a wearing position with respect to a user is based on a detected motion signal and a detected height signal.

In a third aspect, the invention relates a computer program product adapted to carry out the method of the second aspect. The computer program product may be implemented into a computing unit of the sensing device to render the device the functionality of the second aspect of the present invention.

In general the various aspects of the invention may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Embodiments of the present invention relates to a sensing device for detecting a wearing position of the device. The sensing device may be part of a host device with a given functionality where the wearing position of the device is needed for improved operation. Such devices include, but are not limited to, activity sensors and fall detectors.

Figure 1:
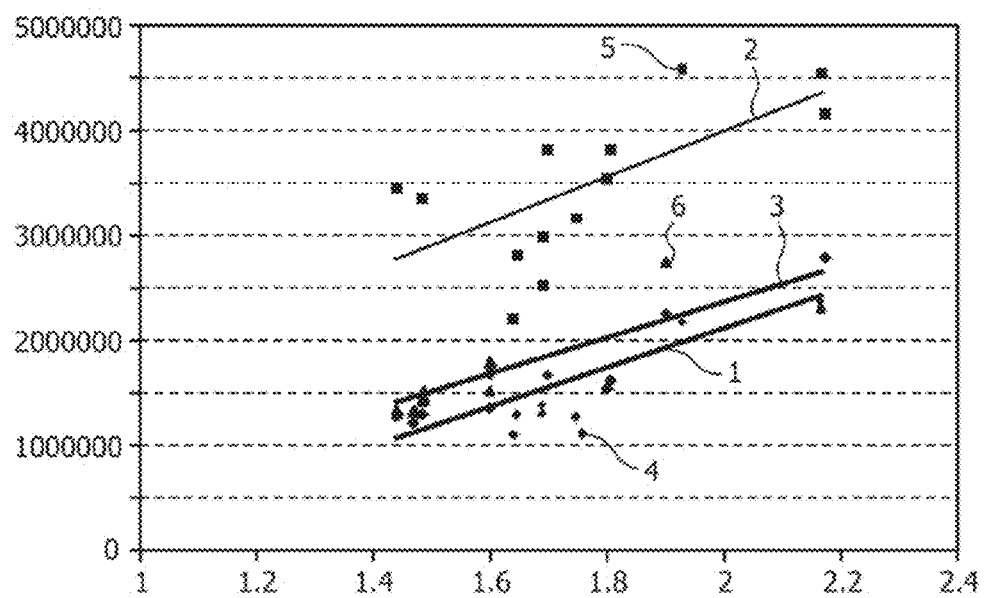
FIG. 1 shows a graph of accumulated acceleration power based on accelerometer data and the corresponding physical activity level based on the doubly-labeled water method.

FIG. 1 as already discussed in the section Background of the Invention, illustrates that calculated activity levels may be dependent upon the assumed wearing position of the activity sensor. Not using the correct wearing position when converting detected movements into a physical activity level may thereby introduce uncertainty in the calculated activity level. In connection with fall detection it is also important to know the correct wearing position. The algorithm used for detecting a fall uses the wearing position together with the detected movement to determine whether or not the detected movement was related to a fall or not. In fall detection is it important to have as low a false alarm rate as possible while not missing any falls that actually happened, and therefore it is important to know the correct wearing position.

Figure 2:
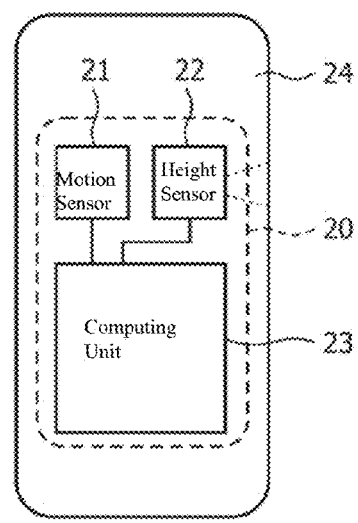
FIG. 2 illustrates an embodiment of a sensing device for detecting a wearing position.

FIG. 2 illustrates an embodiment of a sensing device 20 for detecting a wearing position. The device comprises a motion sensor 21 for detecting a motion signal. The motion sensor is typically a tri-axial accelerometer. The device further comprises a height sensor 22 for detecting a height signal of the sensor location. The height sensor may be an altimeter or a barometer based on measuring an air pressure signal or difference in air pressure. The device further comprises a computing unit 23. The computing unit is connected to the motion sensor and the height sensor for accessing or reading the motion signal and the height signal. Based on the inputs from the motion sensor and height sensor, the computing unit determines the wearing position of the sensing device with respect to a user.

The two sensors are placed very close in the housing so that they measure signals related to movement of the same body part. For example, if the sensing device is attached to the knee, the two sensors should be placed so close that the detected movement is related to the movement of the knee alone and not from movement of adjacent limbs. Thus the proximity of the two sensors should be closer for knee attachment than for chest attachment. To have the freedom of attachment to different body parts, the two sensors should be placed so that the detecting area of the motion sensor and the detecting area of the height sensor are located less than five centimeters from each other. They may also be collocated, located adjacently or fixed to each other.

In an embodiment, the motion sensor 21 measures both inertial accelerations caused by the body movements and gravitational accelerations imposed by the earth's gravity. The height (e.g., pressure) sensor 22 makes use of the air pressure variation when it moves vertically to provide information about altitude change. In an embodiment, the pressure sensor may be calibrated, for instance by setting a reference altitude as the reference level. The air pressure sensor may then measure height or height change with regard to this reference level.

The device is typically made integral with a host device 24, the host device may comprise additional components to the ones shown in FIG. 2. For example, the host device may comprise connector jacks for connection to peripheral equipment, such as connection to an external computing device. The host device may also comprise a display for display of activity level, etc. In embodiments the sensing device and the host device may share components, such as the accelerometer and the height sensor, which may additionally be used for calculating an activity level or other parameters. Likewise the computing unit may be shared between the host device and the sensing device.

Figure 3:
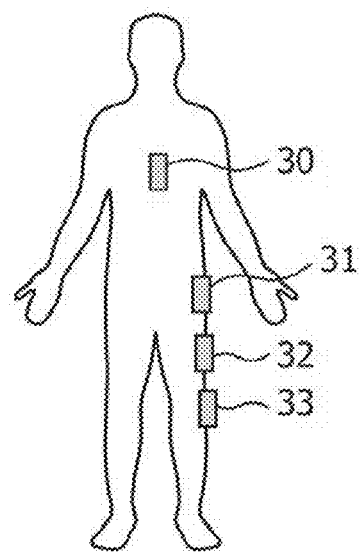
FIG. 3 illustrates examples of attachment positions of the sensing device.

For the recognition of common physical activity types, such as walking, running, cycling, and the assessment of the related energy expenditure, it is desirable to wear the sensing device close to the body trunk instead of extremities like ankle and wrist so that the whole body movement gets recorded. FIG. 3 illustrates examples of attachment positions of the sensing device in this regard. For example the sensing device may be attached at the chest 30, e.g. as a pendant around the neck or attached to a bra; at the hip 31, e.g. clipped to a belt; at the thigh 32, e.g. in the pocket of the trousers; at the knee 33, e.g. by use of a strap. Body positions are not limited to above-mentioned ones, and these are only shown as examples. Moreover, the illustration of several sensing devices 30-33 is not to be interpreted as more than one sensing device is used. In test situations several sensing devices may be attached to one person, however in a typical situation of use, only a single sensing device is used.

Figure 4:
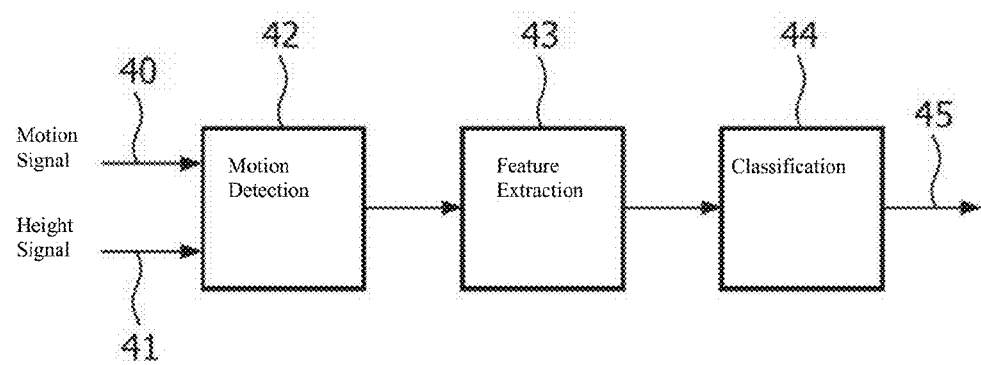
FIG. 4 illustrates a block diagram of an embodiment of an algorithm for detecting the wearing position of the sensing device.

FIG. 4 illustrates a block diagram of an embodiment of an algorithm for detecting the wearing position of the sensing device. The motion signal 40 and height signal 41 are input into a motion detection unit or block 42 implemented in the computing unit of the sensing device. The motion detection block 42 detects the occurrence of a signal transition corresponding to a given type of motion of the user wearing the device, in the motion signal and in the height signal. The motion detection block thus seeks to recognize a specific preselected movement type of the user from one of, or both of, the input signals 40, 41. Once a given preselected type of motion has been recognized or detected, at least one parameter related to the motion signal during the occurrence of the motion of the preselected type is extracted from the motion signal and at least one parameter related to the height signal during the occurrence of the motion of the preselected type is extracted from the height signal in a feature extraction block 43. The extracted parameters are input into a classification block 44 for, based on a classification algorithm, detecting the wearing position 45.

In an embodiment, the computing unit is adapted to monitor the motion signal and/or the height signal to recognize a given or preselected type of motion and to detect that a signal transition corresponding to this given type of motion in the motion signal and/or in the height signal has occurred. The shape of the signal transition is related to a specific movement of the body. In connection with FIGS. 5-7 the signal transition related to a sit-stand movement is used, however other types of movements and related signal transitions can be used as well, such as signal transitions related to walking, to jumping, etc. The recognition of a specific motion can be realized using a stand-alone activity classifier based on both acceleration and altimeter data. In addition, the context of the occurrence of the motion can be used in connection with the recognition. For example, the acceleration data provide both movement (e.g. walking or cycling) and posture (e.g. standing or lying) information of the relevant body part.

FIG. 5 illustrates screen shots showing acceleration and altimeter signals during stand-sit transitions from a test where a subject wore a sensing device at four different locations of the body.

Figure 5A:
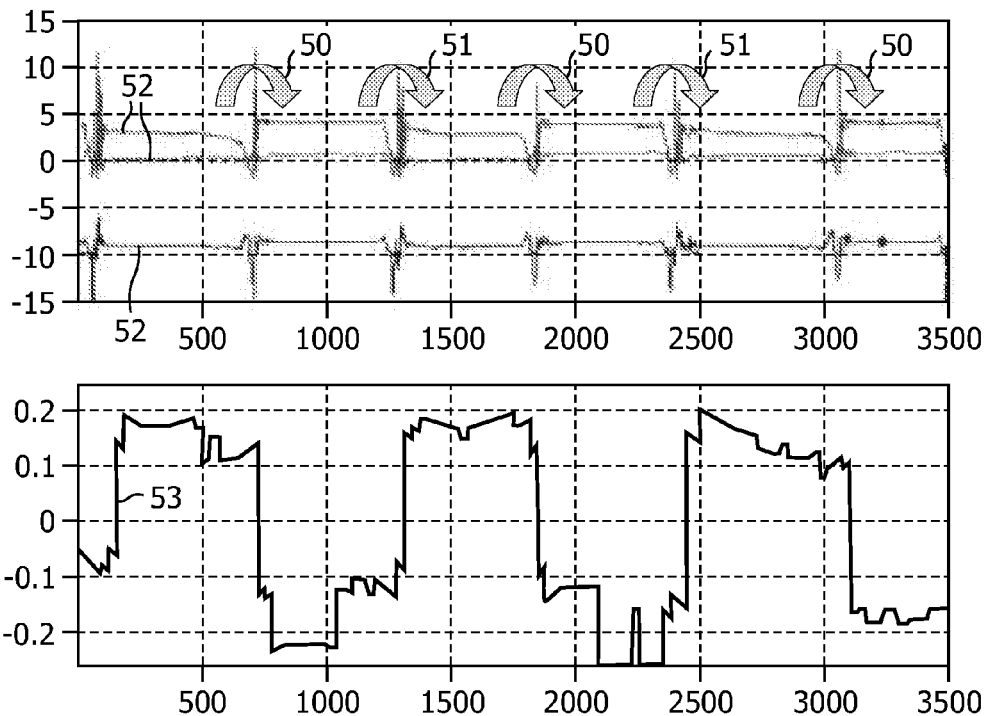
FIGS. 5A-D illustrate screen shots showing acceleration and altimeter signals during stand-sit transitions.
Figure 5B:
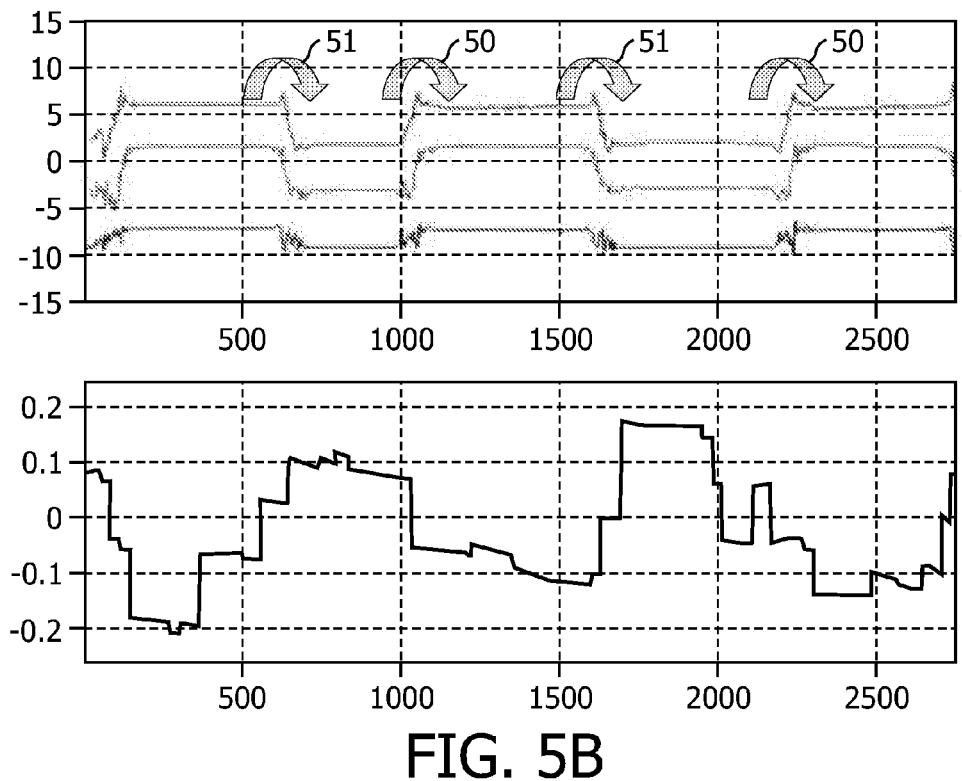
Figure 5C:
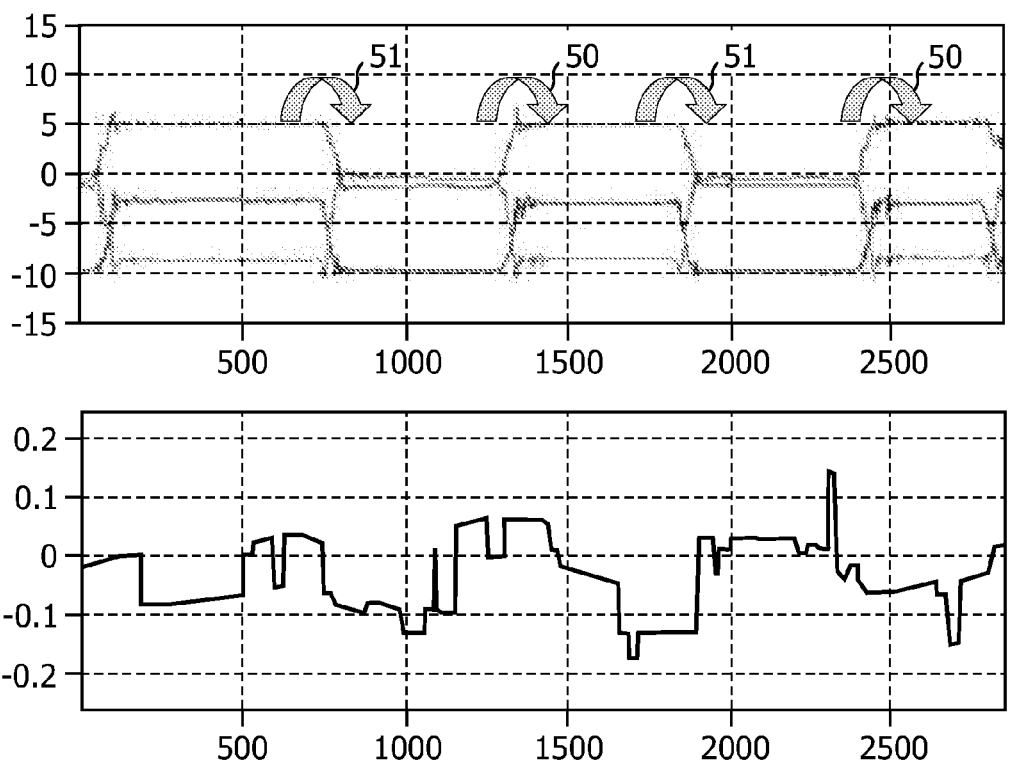
Figure 5D:
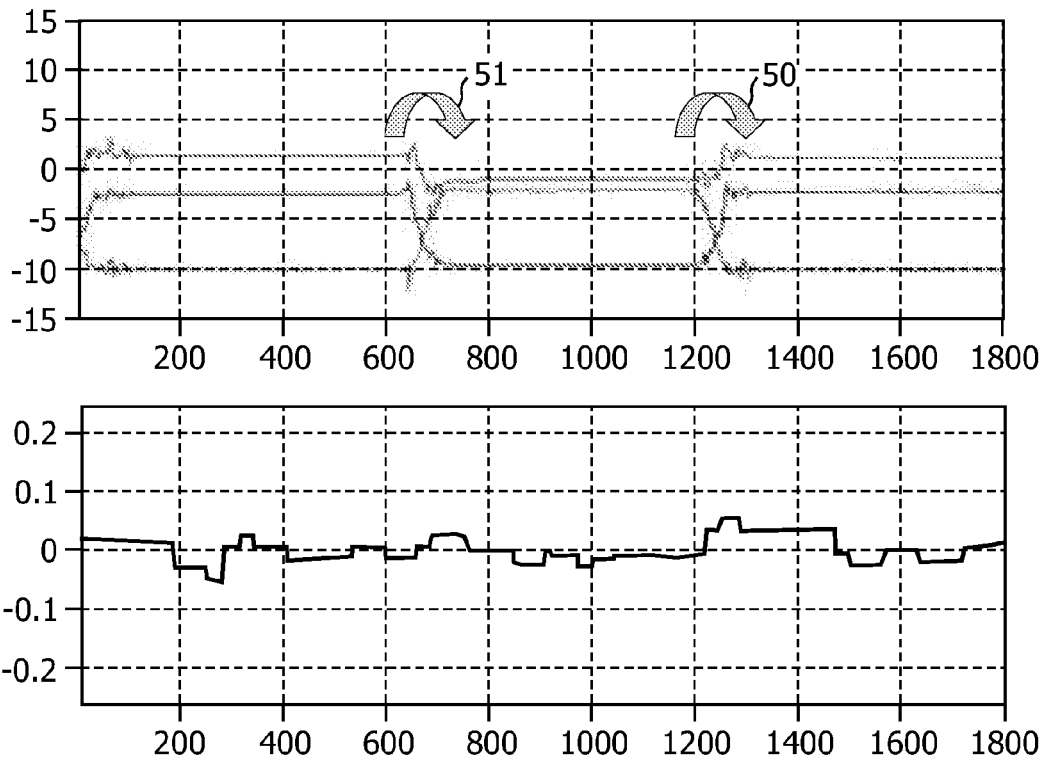

FIGS. 5A to 5D illustrate motion signals 52 (top) and altimeter signals 53 (bottom) measured during consecutive stand-sit transitions. In the plots of the motion signals, the readout from three sensing axes of a tri-axial accelerometer are shown, and stand-to-sit and sit-to-stand transitions are indicated with reference numeral 50 and reference numeral 51 respectively. The altimeter signal (bottom) was first processed with a median filter to remove high frequency spikes without sacrificing the sharp stand-sit transition edges, additionally the DC wander caused by the slow ambient pressure changes (due to the weather) gets removed as well. FIG. 5A illustrates the signals of the sensing device positioned at the chest; FIG. 5B illustrates the signals of the sensing device positioned at the hip; FIG. 5C illustrates the signals of the sensing device positioned at the thigh; and FIG. 5D illustrates the signals of the sensing device positioned at the knee.

Referring back to FIG. 4, the motion detection block 42 monitors the motion signal and the height signal, and once the desired motion type is detected, parameters or signal features are extracted from the signals by the feature extraction block 43. Examples of signal features (parameters) that may be extracted when the desired motion is a stand-sit/sit-stand transition include, but are not limited to, such features as:
1) height change around a transition;
2) orientation change around a transition;
3) acceleration energy around transition;
4) sensor trajectory around transition;
5) difference in height change between stand-to-sit and sit-to-stand transitions;
6) difference in orientation change between stand-to-sit and sit-to-stand transitions.

More specifically, the signal feature reflecting the height change may be defined as:

$$\Delta h = |h_{stand} - h_{sit}|$$

where $h_{stand}$ and $h_{sit}$ denote the altimeter readout during standing and sitting respectively.

They can be sampled at a fixed distance in time, say a couple of seconds, before and after the transition, or calculated as an average value of points sampled before and after the transition. This is to reduce the sensitivity of altimeter readout to noise sources, which often lead to signal fluctuations.

The orientation change may be defined as the angle $\theta$ that the gravitational vector $a^{(g)}$ rotates during a stand-sit transition, calculated as:

$$\theta = a\cos\left(\frac{a_{stand}^{(g)} \cdot a_{sit}^{(g)}}{|a_{stand}^{(g)}||a_{sit}^{(g)}|}\right)$$

where • represents a dot product of two vectors, and || calculates the magnitude of a vector.

Other forms reflecting the difference of two vectors can be also considered, such as the Euclidean distance:

$$d = \|a_{stand}^{(g)} - a_{sit}^{(g)}\|$$

The extraction of features and thereafter the realization of the sensor position detection are dealt with by the sensor positioning classification block 44 (cf. FIG. 4). In an embodiment, the classification is based on the height change and the orientation change as define above.

Figure 6:
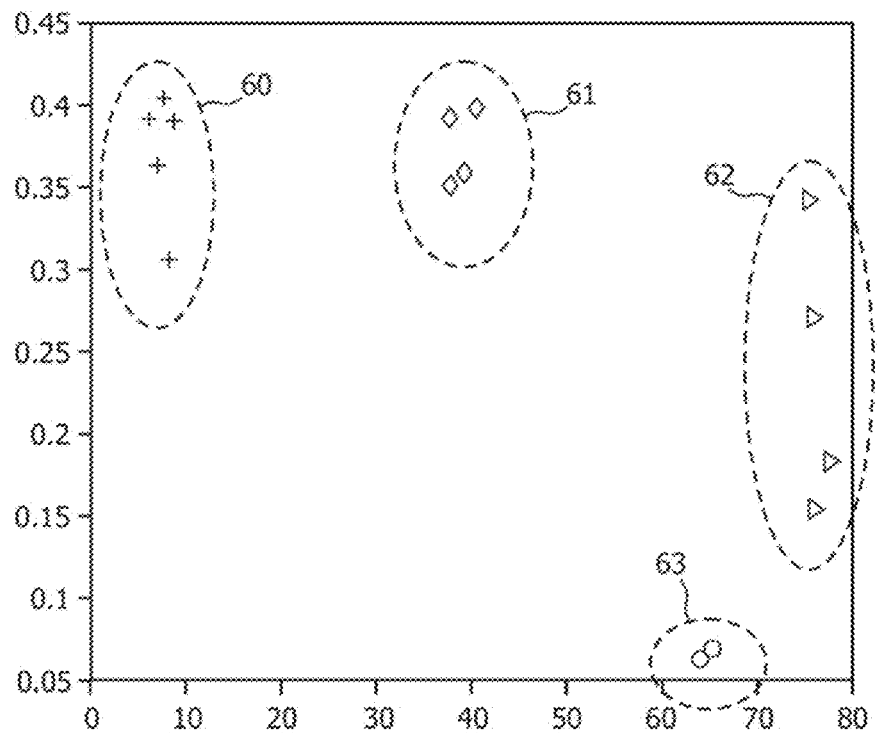
FIG. 6 illustrates a scatter plot of parameters extracted from the motion signal and from the height signal.

FIG. 6 illustrates a plot of parameters extracted from the motion signal and from the height signal in a joint feature space. The plot is in the form of a scatter plot of the height change and the orientation change, with the orientation change in degrees along the horizontal axis and height change in meters along the vertical axis. Each point corresponds to one stand-sit transition; plus indicates chest points 60; diamond indicates hip points 61; triangle indicates thigh points 62; and circle indicates knee points 63. It can be seen that with the orientation change only, thigh points 62 would be difficult to distinguish from knee points 63, whereas with the height change only, the cluster of chest points 60 overlaps with that of hip points 61. In the joint feature space, however, the four clusters are very well separated.

A classifier, such as a decision tree, can be implemented to detect the correct sensor position based on the extracted parameters from the motion signal and the height signal. To obtain a classification algorithm to be used in practical situations, more stand-sit transitions than the ones shown in FIG. 6 need to be collected to establish a sizeable training set. To get good statistics, these transitions are preferably recorded with different sensor wearing positions and cover a wide demographic range of relevant subjects. The classification algorithm may access a database of predefined signal features associated with related wearing positions, and base the classification on a comparison between the predefined signal features of the database and the one or more parameters extracted from the motion signal and the height signal to determine the wearing position of the sensing device.

Dependent upon the specific type of algorithm used, the recognition of the type of the motion may require prior knowledge of a sensor wearing position. In an embodiment, a hypotheses-confirmation structure is implemented based on an initial guess and subsequent confirmation of the guess. In this regard, an initial wearing position may be accessed from a set of possible wearing positions and compared with the detected wearing position. The initial wearing position may in an embodiment be the last detected wearing position, it may be a random guess, it may be detected from preliminary signal analysis, or from other means. If the detected wearing position matches the initial wearing position the detected wearing position is maintained, otherwise a new initial wearing position from the set of possible wearing positions is selected and the new wearing position is detected, and the new initial wearing position and the new detected wearing positions are compared.

Figure 7:
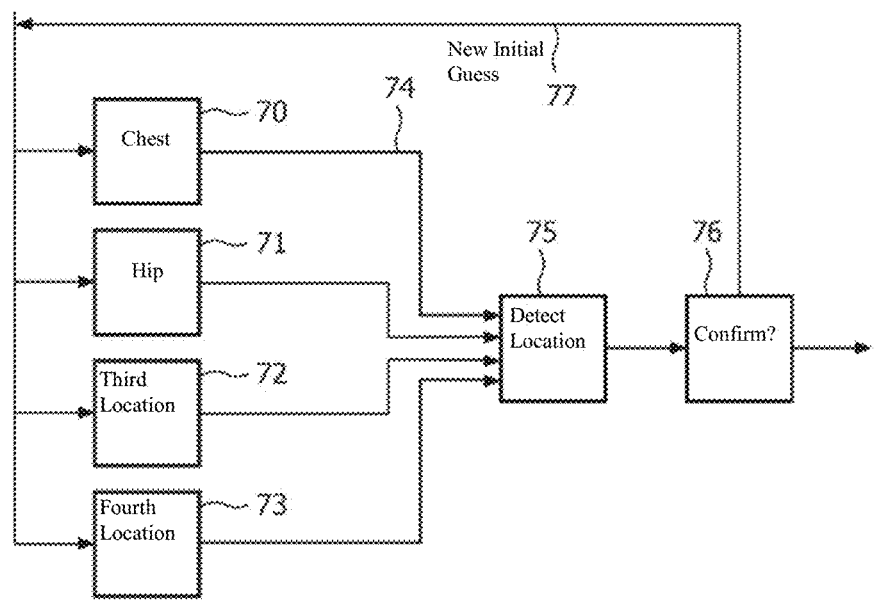
FIG. 7 illustrates a block diagram of an embodiment of an algorithm for implementing a hypotheses-confirmation structure in the scheme for detecting the wearing position.

In an embodiment, the hypotheses-confirmation structure is implemented as schematically depicted in FIG. 7. The blocks 70-73 each determines a sit-stand transition with an initial assumption of the wearing location. More or less blocks are possible depending on the number of possible wearing locations supported by the device. Each of the blocks embody a motion detection block 42 as depicted in FIG. 4, however implemented with a motion detection algorithm detecting a specific type of movement with an assumed device wearing location. The output of these blocks 74 will be a yes or a no. That it, the algorithm used for detecting a sit-stand transition assumes an initial wearing location and monitors the motion signal and/or the height signal until a sit-stand transition is detected.

In an embodiment, the initial guess may be a sit-to-stand transition with chest location 70. If a sit-to-stand transition is detected (output 74 is yes), the block 75 will perform the above-described method for wearing location detection. That is, block 75 implements the feature extraction block 43 and the classification block 44 as depicted in FIG. 4. However, the calculation of the wearing location is only initiated upon a "yes" output 74. The calculation itself does not use the assumed locations, and it simply extracts the parameters to be used for the detection and runs the classification based on these parameters. The block 76 checks whether or not the output of block 75 confirms the assumption of the initial wearing location in the sit-stand detection block 70. If so, a high probability can be assumed for the wearing location result, if not a low probability can be assumed. When there is confirmation the calculated wearing location is assumed, otherwise the result is ignored. If the result is ignored, a new initial guess 77 (e.g. hip location 71) is assumed and the confirmation method is repeated until a confirmed location is achieved; or in the event, that no confirmation is achieved when having tried all four options, then the segment of data is ignored and the method is repeated with the next segment of the data. A new initial guess may also be made if for example too long time is spent in order to detect a specific movement such as a sit-stand transition.

Thus for a given or selected type of movement to be detected, the blocks 70-73 may be run on any candidate segment for this selected type of movement in the sensing data, sequentially. In a first situation, the motion is detected and confirmation is obtained on sensor location, and thus there is no need to run the rest of the blocks if any. In a second situation, the motion is not detected, and in the third the motion is detected but no confirmation is obtained with all four blocks having been executed. For all these situations, the algorithm moves to the next candidate segment of the preselected type of movement.

To improve the detection accuracy further, decision fusion methods can be applied upon the detection over longer times. In this case, intermediate decisions on the wearing position are made, each based on one stand-sit transition. The ultimate decision is then made by means of a certain decision fusion method. For instance, with majority voting, a sensor position appearing most often among the accumulated intermediate decisions wins.

It is envisioned that a more accurate location indication can be achieved when more information is available to the algorithm, like the body length, limb lengths, and chair heights in the case where a sit-stand transition is targeted. Application of a wearing location detection algorithm would be improved by normalization of the detected height change using the body length.

The invention can be implemented in any suitable form including hardware, software, firmware or any combination of these. The invention or some features of the invention can be implemented as computer software running on one or more data processors and/or digital signal processors. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A sensing device configured to detect a wearing position, the sensing device comprising:
   a motion sensor configured to detect a motion signal;
   a height sensor configured to detect a height signal based on air pressure; and
   a computing unit;
   wherein the motion sensor and the height sensor are communicatively connected to the computing unit, and where the computing unit, in response to receiving the motion signal and the height signal based on air pressure, determines the wearing position of the sensing device with respect to a user based on both the motion signal and the height signal based on air pressure.

2. The sensing device of claim 1, wherein the detecting area of the motion sensor and the detecting area of the height sensor are located less than five centimeters from each other.

3. The sensing device of claim 1, wherein the motion sensor is a tri-axial accelerometer.

4. The sensing device of claim 1, wherein the height sensor is an altimeter configured to detect the height signal based on a difference in air pressure.

5. The sensing device of claim 1, wherein the computing unit is further adapted to recognize a preselected type of a motion in the motion signal or in the height signal based on air pressure, and to detect that of the preselected type of motion has occurred in the motion signal and in the height signal based on air pressure.

6. The sensing device of claim 5, wherein the computing unit is further adapted to, subsequent to detecting the preselected type of motion, determine the wearing position from one or more parameters extracted from the motion signal and the height signal based on air pressure measured during the occurrence of the motion of the preselected type.

7. The sensing device of claim 6, wherein the computing unit is adapted to execute a classification algorithm, and where the classification algorithm is adapted to detect the wearing position, based on the one or more parameters extracted from the motion signal and the height signal based on air pressure measured during the occurrence of the motion of the preselected type.

8. The sensing device of claim 7, wherein the classification algorithm is adapted to access a database of predefined signal features, the predefined signal features being associated with related wearing positions, and wherein the classification algorithm is further adapted to perform a comparison between the predefined signal features and one or more parameters extracted from the motion signal and the height signal based on air pressure, so as to determine the wearing position of the sensing device.

9. The sensing device of claim 7, wherein the computing unit is further adapted to access an initial wearing position from a set of possible wearing positions, detecting the wearing position, and compare the detected wearing position to the initial wearing position, if the detected wearing position matches the initial wearing position, the detected wearing position is maintained, otherwise a new initial wearing position from the set of possible wearing positions is accessed and a new wearing position is detected, and the new initial wearing position and the new detected wearing positions are compared.

10. A method for detecting a wearing position of a sensing device, the method comprising:
- detecting, by a motion sensor of a sensing device, a motion signal;
- detecting, by a height sensor of the sensing device, a height signal based on air pressure; and
- calculating, by a computing unit of the sensing device, based on both the motion signal and the height signal based on air pressure, a wearing position of the sensing device with respect to a user.

11. A non-transitory computer readable medium with instructions stored therein which upon execution instruct at least one processor to:
- detect a motion signal from a sensing device;
- detect a height signal based on air pressure from the sensing device; and
- calculate a wearing position of the sensing device with respect to a user based on both the motion signal and the height signal based on air pressure.

12. The sensing device of claim 1, wherein the height sensor configured to detect a height signal based on air pressure uses air pressure variation when the air pressure moves vertically to obtain information about altitude change.

13. The method of claim 10 further comprising:
- recognizing, by the computing unit, a preselected type of a motion in the motion signal or in the height signal based on air pressure;
- detecting, by the computing unit, that the preselected type of motion has occurred in the motion signal and in the height signal based on air pressure; and
- determining, by the computing unit, the wearing position from one or more parameters extracted from the motion signal and the height signal based on air pressure measured during the occurrence of the preselected type of motion.

14. The method of claim 10, wherein the detecting the height signal based on air pressure comprises obtaining air pressure variation when the air pressure moves vertically to obtain information about altitude change.

15. The non-transitory computer readable medium of claim 11, wherein the sensing device comprises a motion sensor configured to detect the motion signal.

16. The non-transitory computer readable medium of claim 11, wherein the sensing device comprises a height sensor configured to detect the height signal.

17. The non-transitory computer readable medium of claim 11, wherein the sensing device comprises a computing unit configured to calculate the wearing position.

18. The non-transitory computer readable medium of claim 11, wherein the processor configured to calculate the wearing position comprises:
- recognizing a preselected type of a motion in the motion signal or in the height signal based on air pressure;
- detecting that the preselected type of motion has occurred in the motion signal and in the height signal based on air pressure; and
- determining the wearing position from one or more parameters extracted from the motion signal and the height signal based on air pressure measured during the occurrence of the preselected type of motion.

19. The non-transitory computer readable medium of claim 11, wherein the processor configured to detect the height signal based on air pressure comprises obtaining air pressure variation when the air pressure moves vertically to obtain information about altitude change.

* * * * *